(12) United States Patent
McNulty et al.

(10) Patent No.: US 6,627,141 B2
(45) Date of Patent: Sep. 30, 2003

(54) METHOD FOR MOLDING A CROSS-LINKED PREFORM

(75) Inventors: Donald E. McNulty, Warsaw, IN (US); Todd Smith, Fort Wayne, IN (US)

(73) Assignee: DePuy Orthopaedics, Inc., Warsaw, IN (US)

(*) Notice: Subject to any disclaimer, the term of this patent is extended or adjusted under 35 U.S.C. 154(b) by 294 days.

(21) Appl. No.: 09/855,794

(22) Filed: May 15, 2001

(65) Prior Publication Data

US 2001/0026033 A1 Oct. 4, 2001

Related U.S. Application Data

(63) Continuation of application No. 09/327,666, filed on Jun. 8, 1999, now Pat. No. 6,245,276.

(51) Int. Cl.$^7$ .......................... B29C 35/08; B29C 41/02
(52) U.S. Cl. ...................... 264/488; 264/322; 264/494
(58) Field of Search ............................... 264/322, 488, 264/494

(56) References Cited

U.S. PATENT DOCUMENTS

| | | |
|---|---|---|
| 3,297,641 A | 1/1967 | Werber et al. |
| 3,352,818 A | 11/1967 | Meyer et al. |
| 3,646,155 A | 2/1972 | Scott |
| 3,671,477 A | 6/1972 | Nesbitt |
| 3,758,273 A | 9/1973 | Johnston et al. |
| 3,944,536 A | 3/1976 | Lupton et al. |
| 4,138,382 A | 2/1979 | Polmanteer |
| 4,390,666 A | 6/1983 | Moriguchi et al. |
| 4,483,333 A | 11/1984 | Wartman |
| 4,518,552 A | 5/1985 | Matsuo et al. |
| 4,539,374 A | 9/1985 | Fenton et al. |
| 4,582,656 A | 4/1986 | Hoffmann |
| 4,655,769 A | 4/1987 | Zachariades |
| 4,668,527 A | 5/1987 | Fujita et al. |
| 4,743,493 A | 5/1988 | Sioshansi et al. |
| 4,747,990 A | 5/1988 | Gaussens et al. |
| 4,816,517 A | 3/1989 | Wilkus et al. |
| 4,876,049 A | 10/1989 | Aoyama et al. |
| 4,888,369 A | 12/1989 | Moore, Jr. |
| 4,902,460 A | 2/1990 | Yagi et al. |
| 4,944,974 A | 7/1990 | Zachariades |
| 5,024,670 A | 6/1991 | Smith et al. |
| 5,037,928 A | 8/1991 | Li et al. |
| 5,130,376 A | 7/1992 | Shih |
| 5,133,757 A | 7/1992 | Sioshansi et al. |
| 5,160,464 A | 11/1992 | Ward et al. |
| 5,160,472 A | 11/1992 | Zachariades |
| 5,180,394 A | 1/1993 | Davidson |
| 5,192,323 A | 3/1993 | Shetty et al. |
| 5,210,130 A | 5/1993 | Howard, Jr. |
| 5,236,563 A | 8/1993 | Loh |
| 5,356,998 A | 10/1994 | Hobes |
| 5,407,623 A | 4/1995 | Zachariades et al. |
| 5,414,049 A | 5/1995 | Sun et al. |
| 5,449,745 A | 9/1995 | Sun et al. |
| 5,466,530 A | 11/1995 | England et al. |
| 5,478,906 A | 12/1995 | Howard, Jr. |
| 5,480,683 A | 1/1996 | Chabrol et al. |
| 5,508,319 A | 4/1996 | DeNicola, Jr. et al. |
| 5,515,590 A | 5/1996 | Pienkowski |
| 5,543,471 A | 8/1996 | Sun et al. |
| 5,549,698 A | 8/1996 | Averill et al. |
| 5,549,700 A | 8/1996 | Graham et al. |
| 5,577,368 A | 11/1996 | Hamilton et al. |
| 5,593,719 A | 1/1997 | Dearnaley et al. |
| 5,609,638 A | 3/1997 | Price et al. |
| 5,645,882 A | 7/1997 | Llanos |
| 5,650,485 A | 7/1997 | Sun et al. |
| 5,674,293 A | 10/1997 | Armini et al. |
| 5,702,448 A | 12/1997 | Buechel et al. |
| 5,702,456 A | 12/1997 | Pienkowski |
| 5,728,748 A | 3/1998 | Sun et al. |
| 5,876,453 A | 3/1999 | Beaty |
| 5,879,388 A | 3/1999 | Pienkowski et al. |
| 5,879,400 A | 3/1999 | Merrill et al. |
| 5,879,407 A | 3/1999 | Waggener |
| 6,017,975 A | 1/2000 | Saum et al. |
| 6,165,220 A * | 12/2000 | McKellop et al. .......... 128/898 |
| 6,168,626 B1 | 1/2001 | Hyon et al. |
| 6,432,349 B1 * | 8/2002 | Pletcher et al. ......... 264/488 X |

FOREIGN PATENT DOCUMENTS

| | | |
|---|---|---|
| BE | A-1001574 A | 12/1989 |
| EP | 0 169 259 A1 | 7/1984 |
| EP | 0 373 800 A1 | 6/1990 |
| EP | 0722973 A1 | 7/1996 |
| EP | 0729981 A1 | 9/1996 |
| EP | 0 737481 A1 | 10/1996 |
| JP | 58-157830 A | 9/1983 |
| JP | A-59 168 050 | 9/1984 |
| JP | A-62 243 634 | 1/1987 |
| JP | A-04 185651 | 7/1992 |
| JP | 04-198242 A | 7/1992 |
| JP | 09 12 22 22 | 5/1997 |
| WO | WO 93/10953 A1 | 11/1991 |
| WO | WO 95/21212 A1 | 8/1995 |
| WO | WO 96/09330 A1 | 3/1996 |
| WO | WO 97/29793 A1 | 8/1997 |
| WO | WO 98/01085 A1 | 1/1998 |
| WO | WO 98/14223 A1 | 4/1998 |

OTHER PUBLICATIONS

"Poly Two Carbon–Polyethylene Composite–A Carbon Fiber Reinforced Molded Ultra–High Molecular Weight Polyethylene", Technical Report, Zimmer (a Bristol–Myers Squibb Company), Warsaw (1977).

Atkinson, J.R. et al., "Silane cross–linked polyethylene for prosthetic applications. Part I. Certain physical and mechanical properties related to the nature of the material", *Biomaterials*, 4:267 (1983).

(List continued on next page.)

*Primary Examiner*—Leo B. Tentoni
(74) *Attorney, Agent, or Firm*—Barnes & Thornburg

(57) ABSTRACT

A method for forming a plastic prosthesis bearing, net-shape bearing or near net-shape bearing is provided. The method includes providing a cross-linked plastic resin preform in a volume sufficient to accommodate the bearing and molding the cross-linked preform. The molding is accomplished by applying heat and pressure to form the preform into a desired solid plastic shape. The heating and pressure is sufficient to melt the plastic resin so that the plastic resin flows under pressure and quench remaining free-radicals.

33 Claims, No Drawings

OTHER PUBLICATIONS

Atkinson, J.R. et al., "Silane cross–liked polyethylene for prosthetic applications. Part II. Creep and wear behavior and a preliminary moulding test", *Biomaterials*, 5:326 (1984).

Bartel, D.L. et al., "The Effect of Comformity, Thickness, and Material on Stresses In Ultra–High Molecular Weight Components for Total Hip Replacement", *J. Bone & Joint Surgery*, 68–A(7):1041 (1986).

Bhateja, S.K., "Radiation–Induced Crystallinity Changes In Pressure–Crystallized Ultra–High Molecular Weight Polyethylene", *J. Macromol. Sci. Phys.*, B22(1): 159 (1983).

Bhateja, S.K. et al., "Radiation–Induced Cyrstallinity Changes in Linear Polyethylene", *J. Polym. Sci. Polym. Phys. Eds.*, 21: 523 (1983).

Bhateja, S.K. et al., "Radiation–Induced Crystallinity Changes in Polyethylene Blends", *J. Mater. Sci.*, 20: 2839 (1985).

Birkinshaw, C. et al., "The Melting Behavior of Irradiated Polymers", *Thermochimica Acta*, 117: 365 (1987).

Bloebaum, R.D. et al., "Investigation of Early Surface Delamination Observed in Retrieved Heat–Pressed Tibial Inserts", *Clin. Orthop.*, 269: 120 (1991).

Bremmer, T. et al., "Peroxide Modification of Linear Low–Density Polyethylene: A Comparison of Dialkyl Peroxides", *J. Appl. Polym. Sci.*, 49: 785 (1993).

Brown, K. J. et al., "The Wear of Ultra–High Molecular Weight Polyethylene with Reference to Its Use in Prostheses", *Plastics in Medicine & Surgery Plastics & Rubber Institute*, London, 2.1 (1975).

Chen, C.J. et al., "Radiation–Induced crosslinking: II. Effect on the crystalline and amorphous densities of polyethylene", *Coll. & Polym. Sci.*, 269: 469 (1991).

Chen, Y.L. et al., "Photocrosslinking of Polyethylene I. Photoinitiators, Crosslinking Agent, and Reaction Kinetics", *J. Polym. Sci., Part A: Polym. Chem.* 27: 4051 (1989).

Chen, Y.L. et al., "Photocrosslinking of Polyethylene. II. Properties of Photocrosslinked Polyethylene", *J. Polym. Sci., Part A; Polym. Chem.*, 27: 4077 (1989).

Connelly, G.M. et al., "Fatigue Crack Propagation Behavior of Ultrahigh Molecular Weight Polyethylene", *J. Orthop. Res.*, 2: 119 (1984).

deBoer, A.P. et al., "Polyethylene Networks Crosslinked in Solution: Preparation, Elastic Behavior, and Oriented Crystallization. I. Crosslinking In Solution", *J. Polym. Sci., Polym. Phys. Ed.*, 14: 187 (1976).

deBoer, J. et al., "Crosslinking of Ultra–High Molecular Weight Polyethylene in the Melt by Means of 2,5–dimethyl–2,5–bis (tert–butyldioxy)–3–hexyne", *Makromol. Chem. Rapid Commun.*, 2: 749 (1981).

deBoer, J. et al., "Crosslinking of Ultra–High Molecular Weight Polyethylene in the Melt by Means of 2,5–dimethyl–2,5–bis (tert–butyldioxy)–3–hexyne: 2. Crystallization Behavior and Mechanical Properties", *Polymer*, 23: 1944 (1982).

deBoer, J. et al., "Crosslinking of Ultra–High Molecular Weight Polyethylene in the Oriented State with Dicumylperoxide", *Polymer*, 25: 513 (1984).

Dijkstra, D.J. et al., "Cross–linking of ultra–high molecular weight polyethylene in the melt by means of electron bean irradiation", *Polymer*, 30: 866 (1989).

Ding Z.Y. et al., "Model Filled Polymers. VI. Determination of the Crosslink Density of Polymeric Beads in Swelling", *J. Polym. Sci., Part B: Poly. Phys.*, 29: 1035 (1991).

Eyerer, P. et al., "Property changes of UHMW polyethylene hip cup endoprostheses during implantation", *J. Biomed. Materials Res.*, 18: 1137 (1984).

Eyerer, P., "Polyethylene", *Concise Encyclopedia of Medical and Dental Implant Materials*, Pergamon Press, Oxford, 271 (1990).

Ferris, B.D., "A quantitative study of the tissue reaction and its relationship to debris production from a joint implant", *J. Exp. Path.*, 71: 367 (1990).

Gielenz G. et al., "Crystalline and supermolecular structures in linear polyethylene irradiated with fast electrons", *Colloid & Polymer Sci.*, 260: 742 (1982).

Grobbelaar, C.J. et al., "The Radiation improvement of Polyethylene Prosthesis", *J. Bone & Joint Surgery*, 60–B(3): 370–374 (1978).

Goodman, S. et al., "Polyethylene wear in knee arthroplasty", *Acta Orthop. Scand.*, 63(3): 358 (1992).

Grood, E.S. et al., "Analysis of retrieved implants: Crystallinity changes in ultrahigh molecular weight polyethylene", *J. Biomedical Materials Res.*, 16: 399 (1982).

Huang, D.D. et al., "Cyclic Fatigue Behaviors of UHMWPE and Enhanced UHMWPE", *Trans. 38$^{th}$ Ann. Mtg., Orthop. Res. Soc.*, 403 (1992).

Kamel, I. et al., "A Model for Radiation–Induced Changes in Ultrahigh–Molecular–Weight–Polyethylene", *J. Polym. Sci., Polym. Phys. Ed.*, 23:2407 (1985).

Kampouris, E.M. et al., "Benzyl Peroxide as a Crosslinking Agent for Polyethylene", *J. Appl. Polym. Sci.*, 34: 1209 (1987).

Kao, Y.H., "Crystallinity in chemically crosslinked low density polyethylenes: 1 Structural and fusion studies", *Polymer*, 27: 1669 (1986).

Katq, K. et al., "Structural Changes and Melting Behavior of γ–Irradiated Polyethylene", *Japanese J. Appl. Phys.*, 20: 691 (1981).

Kunert, K.A. et al., "Structural investigation of chemically crosslinked low density polyethylene", *Polymer*, 22: 1355 (1981).

Kurth, M. et al., "Effects of Radiation Sterilization on UHMW–Polyethylene", *Trans. Third World Biomaterials Congress*, 589 (1988).

Landy, M.M. et al., "Wear of Ultra–high–molecular–weight Polyethylene Components of 90 Retrieved Knee Prostheses", *J. Arthroplasty*, Supplement, 3: S73 (1988).

Lem, K. et al., "Rheological Properties of Polyethylenes Modified with Dicumyl Peroxide", *J. Appl. Polym. Sci.*, 27: 1367 (1982).

Li, S. et al., "Characterization and Description of an Enhanced Ultra High Molecular Weight Polyethylene for Orthopaedic Bearing Surfaces", *Trans. 16$^{th}$ Ann. Soc. Biomaterials Meeting*, Charleston, SC, 190 (1990).

Manley, T.R. et al., "The effects of varying peroxide concentration in crosslinked linear polyethylene", *Polymer*, 12:176 (1971).

McKellop, H. et al., "Friction, Lubrication and Wear of Polyethylene Metal and Polyethylene/Ceramic Hip Prostheses on a Joint Simulator", *Fourth World Biomaterials Congress*, Berlin, Apr., 118 (1992).

Minkova, L., "DSC of γ–irradiated ultra–high molecular weight polyethylene and high density polyethylene of normal molecular weight", *Colloid & Polymer Sci.*, 266: 6 (1988).

Minkova, L. et al., "Blends of normal high density and ultra–high molecular weight polyethylene, γ–irradiated at a low dose", *Colloid & Polymer Sci.,* 268: 1018 (1990).

Nagy, E.V. et al., "A Fourier transform infrared technique for the evaluation of polyethylene orthopaedic bearing materials", *Trans. 16th Ann. Soc. For Biomaterials Meeting,* Charleston, SC 109 (1990).

Narkis, M. et al., "Structure and Tensile Behavior of Irradiation–and Peroxide–Crosslinked Polyethylene", *J. Macromol. Sci.–Phys.,* B26(1): 37 (1987).

Nusbaum, H. J. et al., "The Effects of Radiation Sterilization on the Properties of Ultrahigh Molecular Weight Polyethylene", *J. Biomed. Materials Res.,* 13: 557 (1979).

Oonishi, H. et al., "Improvement of Polyethylene by Irradiation in Artificial Joints", *Radiat, Phys. Chem.,* 39: 495 (1992).

Oonishi, H. et al., "In Vivo and In Vitro Wear Behavior on Weightbearing Surfaces of Polyethylene Sockets Improved by Irradiation in Total Hip Prostheses", *Surface Modification Technologies V,* 101–115 (1992), Sudarsahn T.S. et al., ed. The Institute of Materials.

Painter, P.C. et al., "The Theory of Vibrational Spectroscopy and its Application to Polymeric Materials", Ed. John Wiley & Sons, New York, U.S.A., (1982).

Paul, J. P., "Forces Transmitted by Joints in the Human Body", *Proc. Instn. Mech. Engrs.* 181, Part 3J, Paper 8 (1966).

Qu, B.J. et al., "Photocross–linking of Low Density Polyethylene. I Kinetics and Reaction Parameters", *J. Appl. Polym. Sci.,* 48: 701 (1993).

Qu, B.J. et al., "Photocross–linking of Low Density Polyethylene. II Structure and Morphology", *J. Appl. Polym. Sci.,* 48: 711 (1993).

Rimnac, C.M. et al., "Chemical and Mechanical Degradation of UHMWPE: Report of the Development of an *In Vitro* Test", *J. Appl. Biomaterials,* 5:17 (1994).

Rimnac, C.M. et al., "Observations of Surface Damage and Degradation on Retrieved PCA Knee Implants", *Trans. 38th Ann. Orthopaedic Res. Socieity,* Washington, D.C., 330 (1992).

Rimnac, C.M. et al., "Post–Irradiation Aging of Ultra–High Molecular Weight Polyethylene", *J. Bone & Joint Surgery,* 76–A(7): 1052 (1994).

Roe, R. et al., "Effect of radiation sterilization and aging on ultrahigh molecular weight polyethylene", *J. Biomed. Mat. Res.,* 15: 209 (1981).

Rose, R.M. et al., "On the True Wear Rate of Ultra–High Molecular Weight Polyethylene in the Total Hip Prosthesis", *J. Bone & Joint Surgery,* 62A(4): 537(1980).

Rose, R.M. et al., "Exploratory Investigations in the Structure Dependence of the Wear Resistance of Polyethylene", *Wear,* 77:89 (1982).

Rostoker, W. et al., "The Appearances of Wear on Polyethylene—A Comparison of in vivo and in vitro Wear Surfaces", *J. Biomed. Materials Res.,* 12:317 (1978).

Seedhom, B.B. et al., "Wear of Solid Phase Formed High Density Polyethylene in Relation to the Life of Artificial Hips and Knees", *Wear,* 24: 35 (1973).

Shen, C. et al., "The Friction and Wear Behavior of Irradiated Very High Molecular Weight Polyethylene", *Wear,* 30:349 (1974).

Shinde, A. et al., "Irradiation of Ultrahigh–Molecular–Weight Polyethylene", *J. Polym. Sci., Polym. Phys. Ed.,* 23: 1681 (1985).

Spruiell, J.E. et al., "Methods of Experimental Physics", L. Marton & C. Marton, Eds., Vol 16, Part B Academic Press, New York (1980).

Streicher, R.M., "Ionizing irradiation for sterilization and modification of high molecular weight polyethylenes", *Plastics & Rubber Processing & Applications,* 10: 221 (1988).

Streicher, R.M., "Investigation on Sterilization and Modification of High Molecular Weight Polyethylenes by Ionizing Irradiation", *Beta–gamma,* 1/89:34–43 (1989).

Swanson, S.A.V. et al., "Chapter 3, Friction, Lubrication and Wear", *The Scientific Basis of Joint Replacement,* Pittman Medical Publishing Co., Ltd., (1977).

Wang, X. et al., "Melting of Ultrahigh Molecular Weight Polyethylene", *J. App. Polymer Sci.,* 34:593 (1987).

Wright, T.M. et al., "The effect of carbon fiber reinforcement on contact area, contact pressure, and time–dependent deformation in polyethylene tibial components", *J. Biomed. Materials Res.,* 15:719 (1981).

Zachariades, A.E., "A New Class of UHMWPE Orthopaedic Prosthetic Devices with Enhanced Mechanical Properties", *Trans. Fourth World Biomaterials Congress,* Berlin 623 (1992).

Zhao, Y. et al., "Effect of Irradiation on Crystallinity and Mechanical Properties of Ultrahigh Molecular Weight Polyethylene", *J. Appl. Polym. Sci.,* 50:1797 (1993).

"News You Can Use", Vol. II, No. 2 (May 1996).

"For the Tough Jobs: 1900 UHMW Polymer", Himont, Inc. (1988).

"Abrasion–Resistant 1900 UHMW Polymer", Hercules, Inc. (1979).

"Technical Information: 1900 Ultrahigh Molecular Weight Polymer, General Information and Applications", *Bulletin JPE–101A,* Hercules, U.S.A., Inc., (1989).

"Technical Information: 1900 Ultrahigh Molecular Weight Polymer, Nuclear Radiation Effects", *Bulletin HPE–111,* Himont U.S.A., Inc. (1985).

"Technical Information: 1900 Ultrahigh Molecular Weight Polymer, Effect of Polymer Modification", *Bulletin HPE–116,* Himont U.S.A., Inc. (1987).

"Ultra–High Molecular Weight Polyethylene as Biomaterial In Orthopaedic Surgery", Hogrefe & Huber Publishers (1991).

Appleby, R.W. et al., "Post–gamma irradiation cross–linking of polyethylene tape by acetylene treatment", *J. Material Sci.,* 29: 227–231 (1994).

Higgins, J.C. et al., "Evaluation of Free Radical Reduction Treatments for UHMWPE", *Proceedings of the 42nd Annual Mtg., Orthopaedic Res. Soc.,* Feb. 19–22:485(1996).

Jasty, M. et al., "Marked Improvement in the Wear Resistance of a New Form of UHMPWE in a Physiologic Hip Simulator", *Trans. 43rd Ann. Mtg., Orthopaedic Research Soc.,* San Francisco, CA, Feb. 9–13:785(1997).

Jasty, M. et al., "Marked Improvement in the Wear Resistance of a New Form of UHMPWE in a Physiologic Hip Simulator", *Trans. Soc. Biomaterials,* Vol. XX, p 71, *23rd Ann. Mtg. Soc. for Biomaterials.* New Orleans, Louisana, U.S.A., Apr. 30–May 4:157 (1997).

Streicher, Influence of Ionizing Irradiation in Air and Nitrogen for Sterilization of Surgical Grade Polyethylene for Implants, *Radiat. Phys. Chem.,* Vol. 31, Nos. 4–6: 693–698 (1988).

Pleiss et al., "The Improvement of Polyethylene Prostheses Through Radiation Crosslinking", *Radiat. Phys. Chem.,* 9: 647–652 (1977).

Streicher, "The Behavior of UHMW–PE when Subjected to Sterilization by Ionizing Radiation", Ultra–High Molecular Weight Polyethylene as Biomaterial in Orthopedic Surgery, 66–73 (1990).

Saunders, C. et al., "Radiation Effects on Microorganisms and Polymers for Medical Products", *Medical Device & Diagnostic Industry,* 222:89–22 (1993).

Kang et al., "The Radiation Chemistry of Polyethylene IX. Temperature Coefficient of Cross–linking and Other Effects", *J. Amer. Chem. Society,* 89(9): 1980–1986 (1967).

Rose et al., "Radiation Sterilization and the Wear Rate of Polyethylene", *J. Orthopaedic Res. Society,* 2(4):393–400 (1984).

Oonishi, H. et al., "Super Low Wear Cross–Linked UHM-WPE by Heavy High–Dose Gamma Radiation", *WPOA $2^{nd}$ Congress of Hip Section,* 61 (1996).

Jahan et al., "Combined chemical and mechanical effects on free radicals in UHMWPE joints during implantation", *J. Biomed. Material Res.,* 25: 1005–1006 (1991).

"Standard Practice for Dosimetry in an Electron Bean Facility for Radiation Processing at Energies Between 300 keV and 25 keV", *Am. Soc. for Testing & Materials,* Designation: E1649–94, 870–888 (1995).

Oonishi, H. et al., "The Low Wear of Cross–Linked Polyethylene Socket in Total Hip Prostheses", Encyclopedia Handbook of Biomaterials & Bioengineering, Vol 2, Marcel Dekker, Inc., 1853–1868 (1995).

Atkinson, J. et al., "The nature of silane cross–linked HDPE is discussed. Creep and wear tests indicate its potential as a possible replacement for high molecular weight polyethylene in prostheses", *Polymers in Medicine and Surgery, Conf. Held by Plastics and Rubber Institute and Biological Engineering Soc.,* UK. Sep, P4/1–P4/9 (1986).

Jones, W. et al., Effect of γ Irradiation on the Friction and Wear of Ultrahigh Molecular Weight Polyethylene, *Wear* 70: 77–92 (1981).

Gent, A. et al., "Elastic Behavior, Birefringence, and Swelling of Amorphous Polyethylene Networks", *J. Polymer Sci.* 5: 47–60 (1967).

Zoepfl, F. et al., "Differential Scanning Calorimetry Studies of Irradiated Polyethylene: I. Melting Temperatures and Fusion Endotherms", *J. Polymer Sci. Polym. Chem. Ed.,* 22: 2017–2032 (1984).

Zoepfl, F. et al., "Differential Scanning Calorimetry Studies of Irradiated Polyethylene: II. The Effect of Oxygen", *J. Polymer Sci. Polym. Chem. Ed.,* 22: 2032–2045 (1984).

Mandelkern, L. et al., "Fusion of Polymer Networks Formed from Linear Polyethylene: Effect of Intermolecular Order", contribution from the General Electric Research Laboratory and from the Polymer Structure Section, National Bureau of Standards 82: 46–53 (1960).

Muratoglu, O.K. et al., "A Comparison of 5 Different Types of Highly Crosslinked UHMWPES: Physical Properties and Wear Behavior", $45^{th}$ *Annual Meeting, Orthopaedic Research Society,* Anaheim, CA, Feb. 1–4, 77 (1999).

Muratoglu, O.K. et al., "A Novel Method of Crosslinking UHMWPE to Improve Wear With Little or No Sacrifice on Mechanical Properties", $45^{th}$ *Annual Meeting, Orthopaedic Research Society,* Anaheim, CA, Feb. 1–4, 829 (1999).

Muratoglu, O.K. et al., "Electron Beam Cross Linking of UHMWPE At Room Remperature, A Candidate Bearing Material for Total Joint Arthroplasty", *23rd Annual Meeting of the Society for Biomaterials,* New Orleans, Louisiana, Apr. 30–May 4, 74 (1997).

Matsubara, K et al., "The Wear Properties of High–Density Polyethylene Irradiated by Gamma Rays", *Wear* 10: 214 (1967).

McKellop, H. et al., "Increased Wear of UHMW Polyethylene After Gamma Radiation Sterilization", *Trans.* $26^{th}$ *Ann. ORS,* Atlanta, Georgia, Feb. 5–7 (1980).

McKellop, H., "The Effect of Radiation and Ethylene Oxide Sterilization on the Wear of UHMW Polyethylene", $7^{th}$ *European Conference on Biomaterials,* Sep. 8–11, (1987).

Shen, F.–S. et al., "Irradiation of Chemically Crosslinked Ultrahigh Molecular Weight Polyethylene", *J. Polymer Sci.: Part B: Polymer Phys.* 34: 1063–1077 (1996).

Oka, M. et al., "Wear–Resistant Properties of Newly Improved UHMWPE", *Trans. Fifth World Biomaterials Congress,* Toronto, Canada 520, (May 29–Jun. 2, 1996).

Bellare, A. et al., "Deformation, Morphology and Wear Behavior of Polyethylene", *Trans.* $23^{rd}$ *Ann. Mtg., Soc. Biomaterials,* New Orleans, Louisiana, 75 (Apr. 30–May 4, 1997).

Clarke, I.C. et al., "Simulator Wear Study of High–Dose Gamma–Irradiated UHMWPE Cups", *Trans.* $23^{rd}$. *Ann. Mtg., Soc. Biomaterials,* New Orleans, LA, 71, (Apr. 30–May 4, 1997).

Taylor, G. et al., "Stability of $N_2$ Packaged Gamma Irradiated UHMWPE", *Trans.* $23^{rd}$ *Ann. Mtg., Soc. Biomaterials,* New Orleans, LA, 421, (Apr. 30–May 4, 1997).

Taylor, G. et al., "Stability of $N_2$ Packaged Gamma Irradiated UHMWPE", *Trans.* $43^{rd}$ *Ann. Mtg., Orthopaedic Res. Soc.,* San Francisco, California, 776 (Feb. 9–13, 1997).

McKellop, H. et al., "The Effect of Sterilization Method, Calcium Stearate and Molecular Weight on Wear of UHMWPE Acetabular Cups", *Trans.* $23^{rd}$ *Ann. Mtg., Soc. Biomaterials,* New Orleans, LA, 43 (Apr. 30–May 4, 1997).

McKellop, H. et al., "Effect of Sterilization Method on the Wear Rate of UHMW Polyethylene Acetabular Cups in a Hip Simulator", *Trans.* $43^{rd}$ *Ann. Mtg., Orthopaedic Res. Soc.* San Francisco, CA, 7, 94–16 Feb. 9–13 (1997).

McKellop, H. et al., "Wear of UHMWPE Acetabular Cups After Gamma Sterilization in Nitrogen, Thermal Stabilization and Artificial Aging", *Trans.* $23^{rd}$ *Ann. Mtg., Soc. Biomaterials,* New Orleans, LA, Apr. 30–May 4, 45 (1997).

Wang, A. et al., "Effect of Radiation Dosage on the Wear of Stabilized UHMWPE Evaluated by Hip and Knee Joint Simulators", *Trans.* $23^{rd}$ *Ann. Mtg., Soc. Biomaterials,* New Orleans, LA, 394 (Apr. 30–May 4, 1997).

Wang, A. et al., "Wear Mechanisms and Wear Testing of Ultra–High Molecular Weight Polyethylene in Total Joint Replacements", Hand–Out for Polyethylene Wear in Orthopaedic Implants Workshop, *Trans.* $23^{rd}$ *Ann. Mtg., Soc. Biomaterials,* New Orleans, LA (Apr. 30–May 4, 1997).

Yu, Y.J. et al., "Oxidation of UHMWPE Acetabular Cups After Sterilization and Wear Testing in a Hip Joint Simulator", *Trans.* $43^{rd}$ *Ann. Mtg., Orthopaedic Res. Soc.* San Francisco, CA, 778 (Feb. 9–13, 1997).

Roe, R. et al., "Effect of Radiation Sterilization and Aging on Ultrahigh Molecular Weight Polyethylene", *Journal of Biomedical Materials Research,* 15:209–230 (1981).

Li, S. et al., "Chemical Degradation of Polyethylene in Hip and Knee Replacements", $38^{th}$ *Ann. Mtg., Orthopaedic Research Society,* Washington, D.C., 41, (Feb. 7–20, 1992).

Kurtz, S.M. et al., "Post–Irradiation Aging and The Stresses in UHMWPE Components for Total Joint Replacement", $40^{th}$ *Ann. Mtg., Orthopaedic Research Society,* New Orleans, LA, 584, (Feb. 21–24, 1994).

Lancaster et al., "Friction and Wear", in Jenkins (ed): Polymer Science, 959, 1045, North Holland Publishing Company (1972).

McKellop, H. et al., "Accelerated Aging of Irradiated UHMW Polyethylene for Wear Evaluations", $42^{nd}$ Annual Meeting, Orthopaedic Research Society, Atlanta, Georgia, 483, (Feb. 19–22, 1996).

Blunn, G.W. et al., "The Effect of Oxidation on the Wear of Untreated and Stabilized UHMWPE", $42^{nd}$ Annual Meeting, Orthopaedic Research Society, Atlanta, Georgia, 482, (Feb. 19–22, 1996).

"Duration™ Stabilized UHMWPE: an UHMWPE with Superior Wear and Oxidation Resistance; Technical Development and Scientific Evalation", (Cover sheet and reference page) (Undated).

Sun, D.C. et al., "The Origin of the White Band Observed in Direct Compression Molded UHMWPE Inserts", $20^{th}$ Annual Meeting Society for Biomaterials, 121 (Apr. 5–9, 1994).

Sun, D.C. et al., "On the Origins of a Subsurface Oxidation Maximum and its Relationship to the Performance of UHMWPE Implants", $21^{st}$ Annual Meeting, Society for Biochemicals, San Francisco, CA, 362: (Mar. 18–22, 1995).

Premnath, V. et al., "Melt Irradiated UHMWPE for Total Hip Replacement: Synthesis & Properties", 43rd Annual Meeting, Orthopedic Res. Soc., San Francisco, CA, 91–16, (Feb. 9–13, 1997).

Muratoglu, O.K. et al., "The Effect of Temperature on Radiation Crosslinking of UHMWPE for Use in Total Hip Arthroplasty", $46^{th}$ Annual Meeting, Orthopaedic Res. Soc., Orlando, FL, 0547 (Mar. 12–15, 2000).

D.C. Sun, C. Stark., J. H. Dumbleton, "Development of an Accelerated Aging Method For Evaluation of Long–term Irradiation Effects on UHMWPE Implants", *Polymer Preprints*, Vol. 35, No. 2, Pp. 969–970, (1994).

A.F. Booth, "Industrial Sterilisation Technologies: New and Old trends Shape Manufacturer Choices", *Medical Device & Diagnostic Industry*, Pp. 64–72, Feb. (1995).

B. Hinsch, "Sterilisation Methods for Implants Made of UHMWPE", in *Ultra–High Molecular Weight Polyethylene as Biomaterials in Orthopedic Surgery*, Toronto: Hogrefe & Huber Publishers, Pp. 63–65, (1991).

"Irradiation Effects on Polymers", edited by D.W. Clegg and A.A. Collyer, *Elsevier Applied Science,* London, (1991).

"Radiation Effects on Polymers", edited by R. L. Clough and S. W. Shalaby, *ACS Symposium Series 475,* (1991).

P. Eyerer, M. Kurth, H. A. McKellop and T. Mittimeier, "Characterization of UHMWPE hip cups run on joint stimulators", *J. Biomedical Materials Research*, Vol. 21, pp. 275–291, (1987).

A. Wang, D.C. Sun, C.Stark, J.H. Dumbleton, *Wear,* pp. 181–183:241–249 (1995).

A. Wang, C. Stark, J.H. Dumbleton, "Role of cyclic plastic deformation in the wear of UHMWPE acetabular cups", *Journal of Biomedical Materials Research*, Vol. 29, pp. 619–626, (1995).

* cited by examiner

METHOD FOR MOLDING A CROSS-LINKED PREFORM

CROSS REFERENCE TO RELATED APPLICATION

This application is a continuation of U.S. application Ser. No. 09/327,666, filed Jun. 8, 1999, now U.S. Pat. No. 6,245,276, the specification of which is herein incorporated by reference.

BACKGROUND OF THE INVENTION

The present invention relates to improved bearings for use in orthopaedic implant prosthesis and particularly to methods for making ultra high molecular weight polyethylene (hereinafter, UHMWPE) bearings by molding a cross-linked preform by the application of sufficient heat and pressure.

Such UHMWPE resin is commonly used for bearings in hip, knee, shoulder and elbow prostheses. Typically, the bearings may be formed by direct compression molding processes or by machining the required bearing shapes from mill shapes such as sheet or bar stock. Typically, the stock or the molded bearings are irradiated and subsequently heat treated or heat annealed. The irradiation generates molecular cross-links and free radicals. The free radicals are subsequently eliminated by the heat treating processes.

Reference is made to a number of prior art references as follows: U.S. Patents:

1. U.S. Pat. No. 5,414,049, Non-Oxidizing Polymeric Medical Implant, to Deh-Chuan Sun, et al.
2. U.S. Pat. No. 5,449,745, Non-Oxidizing Polymeric Medical Implant, to Deh-Chuan Sun, et al.
3. U.S. Pat. No. 5,543,471, Non-Oxidizing Polymeric Medical Implant, to Deh-Chuan Sun, et al.
4. U.S. Pat. No. 5,650,485, Non-Oxidizing Polymeric Medical Implant, to Deh-Chuan Sun, et al.
5. U.S. Pat. No. 5,728,748, Non-Oxidizing Polymeric Medical Implant, to Deh-Chuan Sun, et al.
6. U.S. Pat. No. 4,586,995, Polymer and Irradiation Treatment Method, to James C. Randall.
7. U.S. Pat. No. 5,153,039, High Density Polyethylene Article with Oxygen Barrier Properties, to Jay P. Porter, et al.
8. U.S. Pat. No. 5,508,319, High Melt Strength, Ethylene Polymer, Process for Making It, and Use Thereof, to Anthony J. DeNicola, Jr. et al.
9. U.S. Pat. No. 3,352,818, Stability of Polyolefines, to Gerhard Meyer, et al.
10. U.S. Pat. No. 5,577,368, Method for Improving Wear Resistance of Polymeric Bioimplantable Components, to John V. Hamilton, et al.
11. U.S. Pat. No. 5,753,182, Method for Reducing the Number of Free Radicals Present in Ultrahigh Molecular Weight Polyethylene Orthopedic Components, to Joel Higgins.
12. U.S. Pat. No. 5,709,020, Method for Reducing the Generation of Wear Particulates From an Implant, to David A. Pienowski, et al.
13. U.S. Pat. No. 5,702,456, Implant Having Reduced Generation of Wear Particulates, to David A. Pienowski.
14. U.S. Pat. No. 5,515,590, Method for Reducing the Generation of Wear Particulates From an Implant, David A. Pienowski.
15. U.S. Pat. No. 5,593,719, Treatments to Reduce Frictional Wear Between Components Made of Ultra-High Molecular Weight Polyethylene and Metal Alloys, Geoffrey Deamaley, et al.
16. U.S. Pat. No. 4,366,618, Bone Connective Prosthesis Adapted to Maximize Strength and Durability of Prostheses—Bone Cement Interface; and Methods of Forming Same, to Simon Raab.
17. U.S. Pat. No. 5,014,494, Method of Sterilizing Medical Articles, to Robert D. George.
18. U.S. Pat. No. 5,137,688, Irradiated Articles Molded From Polycarbonate'Polyamide Blends, to James L. DeRudder.
19. U.S. Pat. No. 5,879,400, Melt-Irradiated Ultra High Molecular Weight Polyethylene Prosthetic Devices, to Edward W. Merrill et al.
20. U.S. Pat. No. 6,017,975, Process for Medical Implant of Cross linked Ultrahigh Molecular Weight Polyethylene Having Improved Balance of Wear Properties and Oxidation, to Kenneth Ashley Saum, et al. Foreign Patents
21. E.P. Patent No. 0722973 A1, Chemically Crosslinked Ultrahigh Molecular Weight Polyethylene for Artificial Human Joints, to Ron Salovey, et al.
22. W.O. Patent No. 97/29793, Radiation and Melt Treated Ultra High Molecular Weight Polyethylene Prosthetic Devices, to W. Merrill, et al.
23. W.O. Patent No. 98/01085, Crosslinking of Polyethylene for Low Wear Using Radiation and Thermal Treatments, to Fu-Wen Shen, et al.

The above references teach the general concepts involved in forming or consolidating UHMWPE resin directly into a part or a stock form from which the part is made, gamma or other irradiation of the part or the stock form and subsequent heat treating (annealing or remelting) of the part or stock form. The disclosures of these above-listed references are incorporated herein for purposes of establishing the nature of UHMWPE resin, the irradiation steps and options and the heat treating steps and options. Applicant also incorporates by reference U.S. application Ser. No. 09/328,080, filed Jun. 8, 1999, titled CROSS-LINKED MOLDED PLASTIC BEARINGS naming Todd Smith and Donald McNulty as coinventors.

SUMMARY OF THE INVENTION

The present invention is directed to a method for molding a bearing from a preform which has previously been cross-linked by obtaining such a preform and placing it in a press mold defining the desired bearing shape or near net shape and applying heat and pressure in the mold to form the bearing. The preform may be produced from irradiated polymer resin to form cross-links and free radicals followed by a molding process as taught by U.S. application Ser. No. 09/328,080, filed Jun. 8, 1999, titled CROSS-LINKED MOLDED PLASTIC BEARINGS naming Todd Smith and Donald McNulty as coinventors incorporated herein. In some embodiments, the preforms may be made from consolidated UHMWPE stock which has been irradiated. Also, in some embodiments, the irradiated UHMWPE preforms may already be heat treated to quench the free radicals.

The present invention is designed to reduce the amount of wear debris generated from UHMWPE bearings. Such wear debris has been associated with bone and soft tissue deterioration leading to implant loosening, which may necessitate even revision surgery. The present invention is also to improve the wear resistance of UHMWPE bearings.

Additional features of the present invention will become apparent to those skilled in the art upon consideration of the following detailed description of preferred embodiments exemplifying the best mode of carrying out the invention as presently perceived.

DESCRIPTION OF THE PREFERRED EMBODIMENT(S)

The present invention involves producing a cross-linked orthopaedic implant, such as a bearing component by molding a work piece which has been cross-linked by the application of heat and pressure in a mold defining the shape or near net shape of the bearing. The process of the present invention may be used to mold net-shape bearings directly to provide a finish which is satisfactory for an articular (bearing) surface. The term preform is intended to define a plastic resin work piece that is derived from an unfinished plastic resin stock form, unlimiting examples of which include billets, bar stock, and sheets. It is appreciated that the preform of the present invention may be formed from a wide variety of crude or processed plastic resins suitable for use in orthopaedics, that can be converted by manufacture, processing, or combination into a finished bearing, net-shape bearing, or near net-shape bearing. The term "net-shape" is intended to define a shape that is the final shape of the bearing to be used in the implant. "Near net-shape" requires some degree of machining to produce the final bearing. It is believed that smoother bearing surfaces can be made by molding processes than by machining processes.

The preform of the present invention is formed from a plastic resin stock form that has been irradiated previously to form cross-links. The stock form may be formed from an olefinic resin and preferably an UHMWPE resin. Preferably, the stock form is irradiated with gamma rays at a dose of about 2 to 50 Mrads. This stock form may then be machined into a preform of a size and mass suitable to be placed into a net shape compression molding die. The irradiation process may be performed under vacuum, in an inert atmosphere to eliminate oxygen, or in an oxygen reduced atmosphere. It is also appreciated that the present disclosure contemplates radiating the preform.

The molding process, which may be performed under vacuum or oxygen free atmosphere, may involve pressures from 1,000 to 70,000 psi and set point temperatures of 275° to 500° Fahrenheit. The resulting work piece is either the actual desired bearing configuration or blank that can be machined subsequently to produce the desired bearing geometry. It will be appreciated, however, that acceptable results may be achieved when either or both the irradiation process and the molding process are carried out under atmospheric conditions, i.e., with some oxygen present. This may well be the case for certain bearing configurations.

One embodiment of the present invention relates to a method for forming a plastic prosthesis bearing, net-shape bearing, or near net-shape bearing. The method comprises the steps of providing cross-linked plastic resin preform in a volume sufficient to accommodate the bearing and molding the cross-linked preform by applying heat and pressure to form the preform into a desired solid plastic shape. The heating is sufficient to melt the plastic resin preform so that it will flow under pressure.

The providing step may comprise cross-linking a plastic resin stock form by subjecting it to ionizing radiation (about 2 to 50 Mrads, preferably about 5 to 10 Mrads) such as gamma radiation. Preferably, the bar stock is stored in a vacuum, oxygen-free container or low oxygen environment or heat processed at or above the melting point of the polymer to quench remaining free-radicals before it is cut into a preform shape. This preform may or may not be similar to the final net shape part. It need only be of a shape and size that will fit into the dies of compression molding equipment.

The preform is placed into the compression dies. The molding chamber is preferably brought under vacuum and then subjected to heat (about 275° F. to 500° F., preferably about 400° F.) and pressure (about 1000 to 70,000 psi, more preferably about 1000 to about 2500 psi, and most preferably about 2500 psi). The heat, pressure, and molding time are such as to force the preform to conform to the shape of the dies. Additionally, in the instance where the preform contains free radicals, the preform is held at temperature for sufficient time to allow quenching of the free radicals by forming more molecular chain cross-links. The press is then cooled to below the polymer melting point and the net shape bearing is removed from the compression molding press.

A more complete understanding of the present invention can be obtained by referring to the following illustrative examples of the practice of the invention, which examples are not intended, however, to be unduly limitative of the invention.

EXAMPLE 1

A ram extruded bar stock (PolyHi, Ft. Wayne, Ind.) of IUHMWPE polymer resin (GUR 1050 from Ticona, Frankfurt Germany) was acquired. The bar stock was placed into a foil bag and placed under vacuum for a period of time sufficient to produce a substantially oxygen free environment. The foil bag and bar stock were then irradiated with gamma rays at a dose of about 5 to 10 Mrads.

The free-radical containing bar stock was removed from the bag and machined to a preform of a size and mass suitable to be placed into a net shape compression molding die. The resulting machined preform was placed into a die cavity of the molding press. The cavity with the machined preform was evacuated to remove oxygen. About 2500 psi pressure was then applied and the temperature was raised to about 400° F. for a time of about 40 minutes to quench free radicals. The mold was allowed to cool to room temperature where the resulting net shape molded part was removed from the die cavity.

EXAMPLE 2

A ram extruded bar stock (PolyHi, Ft. Wayne, Ind.) of UHMWPE polymer resin (GUR 1050 from Ticona, Frankfurt Germany) was acquired. The bar stock was placed into a foil bag and placed under vacuum for a period of time sufficient to produce a substantially oxygen free environment. The foil bag and bar stock were then irradiated with gamma rays at a dose of about 5 to 10 Mrads.

The free radical containing bar was removed from the bag and placed into a vacuum oven which was subsequently brought under vacuum. To quench substantially all free radicals, the temperature of the vacuum oven was raised to above the melting point of the bar stock, (about 310° F.) for about 24 hours and then brought to room temperature.

The bar stock was then machined to form a preform having a size and mass suitable to be placed into a net shape compression molding die. The machined preform was placed into a die cavity of the molding die. The cavity with the machined preformed was evacuated to remove oxygen. About 2500 psi pressure was then applied and the temperature was raised to about 400° F. for a time of about 40 minutes. The mold was allowed to cool to room temperature where the resulting net shape molded part was removed from the die cavity.

It is thought that the method for forming a plastic prosthesis bearing, net-shape bearing or near net-shape bearing by the present invention and many of its attendant advantages will be understood from the foregoing description and it will be apparent that various changes may be made without departing from the spirit and scope of the invention or sacrificing all of its material advantages, the form hereinbefore described being merely a preferred or exemplary embodiment thereof.

What is claimed is:

1. A method for forming a plastic prosthesis bearing, near net-shape bearing, or net-shape bearing, the method comprising the steps of:

providing an irradiated plastic preform, said preform having a volume sufficient to accommodate the bearing, near net-shape bearing, or net-shape bearing, and molding the irradiated preform by applying heat and pressure to form the preform into a desired shape, the heating being sufficient to cross-link the plastic and quench free radicals present in the preform, the heating also being sufficient to melt the plastic so that it will flow under pressure.

2. The method of claim 1 wherein the molding step involves pressure of about 1000 to about 70,000 psi.

3. The method of claim 1 wherein the molding step involves pressure of about 1000 to about 10,000 psi.

4. The method of claim 1 wherein the molding step involves pressure of about 1000 to about 5,000 psi.

5. The method of claim 1 wherein the heating step involves a temperature of about 275° F. to about 500° F.

6. The method of claim 1 wherein involves a temperature of about 275° F. to about 400° F.

7. The method of claim 1 wherein the heating step involves a temperature of about 400° F.

8. The method of claim 1 wherein the molding step involves maintaining the application of heat for a time sufficient to cross-link the plastic and quench free radicals present in the preform.

9. The method of claim 8 wherein the molding step involves a time of about 40 minutes.

10. The method of claim 1 wherein the plastic preform comprises an olefinic plastic resin.

11. The method of claim 10 wherein the olefinic plastic resin is ultrahigh molecular weight polyethylene.

12. The method of claim 1 wherein the molding step is carried out in an oxygen-reduced atmosphere.

13. The method of claim 1 wherein the molding step is carried out in a vacuum.

14. A method for forming a plastic prosthesis bearing, near net-shape bearing, or net-shape bearing, the method comprising the steps of:

irradiating a plastic preform with a dose of radiation, said preform having a volume sufficient to accommodate the bearing, near net-shape bearing, or net-shape bearing, and molding the irradiated preform by applying heat and pressure to form the preform into a desired shape, the heating being sufficient to cross-link the plastic and quench free radicals present in the preform, the heating also being sufficient to melt the plastic so that it will flow under pressure.

15. The method of claim 14 wherein the irradiating step involves a radiation dose of about 2 to about 50 Mrads.

16. The method of claim 14 wherein the irradiating step involves a radiation dose of about 5 to about 10 Mrads.

17. The method of claim 14 wherein the radiation dose is a dose of gamma radiation.

18. The method of claim 14 wherein the irradiating step is carried out in an oxygen-reduced atmosphere.

19. The method of claim 14, wherein the irradiating step is carried out in a vacuum.

20. The method of claim 14 wherein the molding step involves pressure of about 1000 to about 10,000 psi.

21. The method of claim 14 wherein the molding step involves pressure of about 1000 to about 5,000 psi.

22. The method of claim 14 wherein the heating step involves a temperature of about 275° F. to about 400° F.

23. The method of claim 14 wherein the heating step involves a temperature of about 400° F.

24. The method of claim 14 wherein the molding step involves maintaining the application of heat for a time sufficient to cross-link the plastic and quench free radicals present in the preform.

25. The method of claim 14 wherein the plastic preform comprises an olefinic plastic resin.

26. The method of claim 25 wherein the olefinic plastic resin is ultrahigh molecular weight polyethylene.

27. A method for forming a plastic prosthesis bearing, near net-shape bearing, or net-shape bearing, the method comprising the steps of:

irradiating an ultrahigh molecular weight polyethylene preform with a dose of radiation, said preform having a volume sufficient to accommodate the bearing, near net-shape bearing, or net-shape bearing, and molding the irradiated preform by applying heat and pressure to form the preform into a desired shape, the heating being sufficient to cross-link the ultrahigh molecular weight polyethylene and quench free radicals present in the preform, the heating also being sufficient to melt the ultrahigh molecular weight polyethylene so that it will flow under pressure.

28. The method of claim 27 wherein the irradiating step involves a radiation dose of about 5 to about 10 Mrads.

29. The method of claim 27 wherein the radiation dose is a dose of gamma radiation.

30. The method of claim 27 wherein the molding step involves pressure of about 1000 to about 5,000 psi.

31. The method of claim 27 wherein the heating step involves a temperature of about 275° F. to about 400° F.

32. The method of claim 27 wherein the heating step involves a temperature of about 400° F.

33. The method of claim 27 wherein the molding step involves maintaining the application of heat for a time sufficient to cross-link the plastic and quench free radicals present in the preform.

\* \* \* \* \*